(12) United States Patent
Urazoe et al.

(10) Patent No.: US 7,339,071 B2
(45) Date of Patent: Mar. 4, 2008

(54) ARYL ETHYNYL PHTHALIC ACID DERIVATIVE AND METHOD FOR PRODUCING THE SAME

(75) Inventors: Daisuke Urazoe, Kanagawa (JP); Hideto Mori, Kanagawa (JP); Katsuyoshi Yamakawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 11/088,728

(22) Filed: Mar. 25, 2005

(65) Prior Publication Data
US 2005/0215820 A1   Sep. 29, 2005

(30) Foreign Application Priority Data
Mar. 25, 2004  (JP) ............................. 2004-090235
Aug. 9, 2004   (JP) ............................. 2004-232675

(51) Int. Cl.
C07C 69/80 (2006.01)
(52) U.S. Cl. ...................................................... 560/54
(58) Field of Classification Search ................. 560/54
See application file for complete search history.

(56) References Cited

U.S. PATENT DOCUMENTS 5,185,454 A   2/1993 Bader et al.
5,567,800 A   10/1996 Hergenrother et al.

FOREIGN PATENT DOCUMENTS

JP   11-180970 A   7/1999
JP   2003-73372 A   3/2003

OTHER PUBLICATIONS

T. Takekoshi, "High Temperature Thermoset Polyimides Containing Disubstituted Acetylene End Groups", Polymer, vol. 35, No. 22, 1994, pp. 4874-4880.
P. M. Hergenrother, et al., "Chemistry and Properties of Imide Oligomers End-Capped With Phenylethynyphthalic Anhydrides", Polymer, vol. 35, No. 22, 1994, pp. 4857-4864.
J. G. Smith, Jr., et al., "Chemistry and Properties of Phenylethynyl Phthalic Anhydride Imide Oligomers", Polymer Preprints, vol. 35, 1995, pp. 353-354.
Database. Caplus Online! Chemical Abstracts Service, Columbus, Ohio, US; Blatchly, Richard A. et al: "Theoretical Study of Helix Formation in Substituted Phenylene Ethynylene Oligomers", STN Data base Accession No. 2003:832966, RN:637357-70-1 for Journal of Organic Chemistry, 68(23), 8780-8785(2003).
J. A. Johnston, F. M. Li, F. W. Harris and T. Takekoshi, Synthesis and characterization of imide oligomers end-capped with 4-(phenylethynyl)phthalic anhydrides; Polymer, vol. 35, No. 22, 1994, pp. 4865-4873.

*Primary Examiner*—Taofiq Solola
(74) *Attorney, Agent, or Firm*—Sughrue Mion, PLLC

(57) ABSTRACT

The invention provides an aryl ethynyl phthalic acid and derivatives thereof (including fluorine-containing compounds) represented by Formulae 1, 3, 5, 4A and 5A including the structure of Formula 2, and method of producing these compounds, in which an aryl ethynyl phthalic anhydride is formed by subjecting an aryl phthalic acid to ring closing:

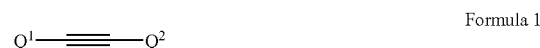

Formula 1

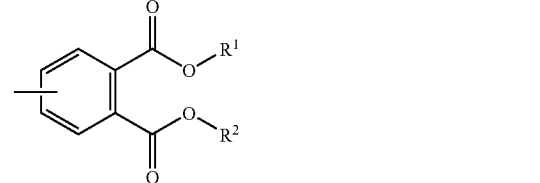

Formula 2

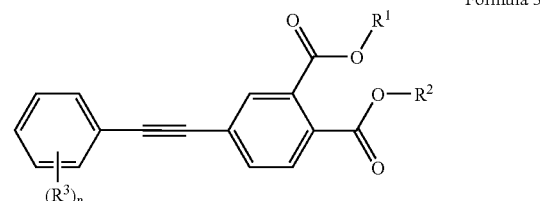

Formula 3

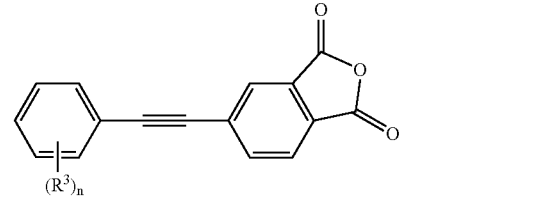

Formula 5

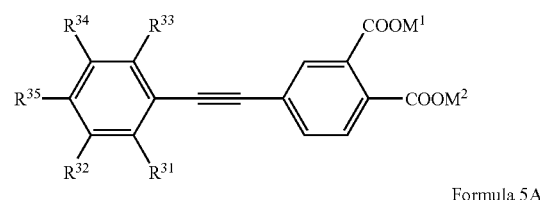

Formula 4A

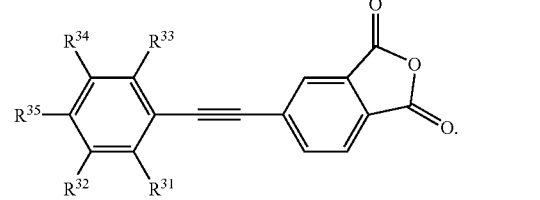

Formula 5A

10 Claims, No Drawings

ARYL ETHYNYL PHTHALIC ACID DERIVATIVE AND METHOD FOR PRODUCING THE SAME

CROSS-REFERENCE TO RELATED APPLICATIONS

This application claims priority under 35 USC 119 from Japanese patent application Nos. 2004-90235 and 2004-232675, the disclosures of which are incorporated by reference herein.

BACKGROUND OF THE INVENTION

1. Field of the Invention

The present invention relates to novel aryl ethynyl phthalic acid derivatives useful for functional materials such as medical and agricultural intermediates and liquid crystal and electronic materials, and to a method for producing the aryl ethynyl phthalic acid derivatives.

2. Description of the Related Art

Aryl ethynyl phthalic acid derivatives are important compounds as the starting materials of functional materials such as medical and agricultural intermediates and liquid crystal and electronic materials and, particularly, have recently received attention as subjects of research relating to various types of functional materials which utilize a carbon-carbon triple bond present in a molecule. For example, phenyl ethynyl acid anhydrides are used as terminal end-blocking agents which impart thermal curability, thermal resistance and acid resistance to polyimide oligomers as described in, for example, U.S. Pat. No. 5,567,800; Polymer, vol. 35, pp. 4874 to 4880, 1994 (hereinafter, referred to also as "Non-Patent Document 1"); ibidem, vol. 35, pp. 4857 to 4864, 1994 ("Non-Patent Document 2"); and Functional Materials, vol. 20, No. 12, pp. 33 to 40, 2000. Further, various types of method for producing phenyl ethynyl phthalic anhydrides are described in, for example, JP-A Nos. 11-180970 ("Patent Document 2") and 2003-73372 ("Patent Document 3"), High Performance Polymer, vol. 6, p. 423, 1994; and Polymer Preprints, vol. 35, p. 353, 1995. However, these are not always satisfactory in terms of yield, efficiency or purity.

Accordingly, development of a novel compound in which performance required for a functional material such as a terminal end-blocking agent is improved and of a method for producing a phenyl ethynyl phthalic anhydride with high purity and high yield are in high demand.

Fluorine-containing aryl ethynyl phthalic acid, an alkali metal salt of fluorine-containing aryl ethynyl phthalic acid and fluorine-containing aryl ethynyl phthalic anhydride have been reported in an extremely small number (see, for example, Non-Patent Document 1). Accordingly, in terms of using these compounds as raw materials to provide resin materials with the desired properties, the range of choice is limited.

SUMMARY OF THE INVENTION

The present invention provides aryl ethynyl phthalic acid derivatives useful for functional materials such as medical and agricultural intermediates and liquid crystal and electronic materials and, in particular, provides aryl ethynyl phthalic acid derivatives used as terminal end blocking materials having superior characteristics useful for these materials. Further, the present invention provides a novel compound which is useful for producing aryl ethynyl phthalic acid derivatives and which is stably produced on an industrial scale, and provides a method for producing the aryl ethynyl phthalic acid derivatives by using the compound.

According to research conducted by the present inventors on phenyl ethynyl phthalic anhydrides, it has been found that the quality of a phenyl ethynyl phthalic anhydride used as a terminal end-blocking material for a polyimide remarkably affects the performance and physical properties of resin materials. For example, it has been found that when a polyimide resin is produced by using phenyl ethynyl phthalic anhydride which is produced by the methods as described in JP-A Nos. 11-180970 and 2003-73372, slightly soluble components may be formed or foam may be formed during thermal molding or curing, so that the resin cannot be stably produced. Namely, the methods that have been reported are not advantageous in terms of the quality assurance of the desired product and the process quality assurance in the post-processing step. Accordingly, a technique which can consistently produce an aryl ethynyl phthalic anhydride with high purity in a substantial quantity has strong been required.

In view of the above, the present inventors conducted intensive research and, as a result, succeeded in synthesizing of a novel compound having a phthalic acid diester structure and found a method for producing an aryl ethynyl phthalic anhydride by using the novel compound, to thereby achieve the present invention.

Namely, the invention is as described below.

A first aspect of the invention is to provide an aryl ethynyl phthalic acid diester compound, represented by the following Formula 1:

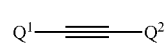

Formula 1 wherein $Q^1$ and $Q^2$ are different from each other; $Q^1$ represents a substituted or unsubstituted aryl group; and $Q^2$ represents a group represented by the following Formula 2:

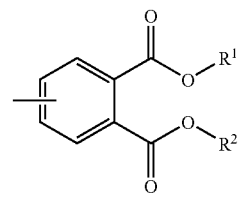

Formula 2 wherein $R^1$ and $R^2$ each independently represent an alkyl group, a cycloalkyl group or an aryl group.

A second aspect of the invention is to provide the aryl ethynyl phthalic acid diester compound of the first aspect of the invention, wherein $R^1$ and $R^2$ in Formula 2 each independently represent an alkyl group having 1 to 8 carbon atoms, a cycloalkyl group or an aryl group.

A third aspect of the invention is to provide an aryl ethynyl phthalic acid diester compound, represented by the following Formula 3:

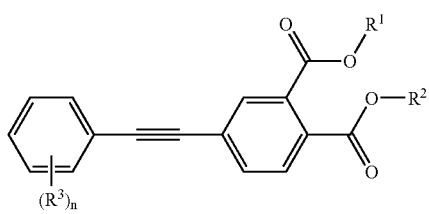

Formula 3 wherein $R^1$ and $R^2$ each independently represent an alkyl group having 1 to 8 carbon atoms, a cycloalkyl group or an aryl group; $R^3$ represents a halogen atom, a hydroxyl group, an alkyl group having 1 to 10 carbon atoms, an aryl group having 6 to 10 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms or a perfluoroalkoxy group having 1 to 6 carbon atoms; n represents an integer of from 0 to 5; and when n represents 2 or more, such that $R^3$ is present in plurality, each $R^3$ may be the same as or different from any other $R^3$ or linked thereto to form a ring.

A fourth aspect of the present invention is to provide a method for producing an aryl ethynyl phthalic anhydride represented by the following Formula 5, wherein an aryl ethynyl phthalic acid compound represented by the following Formula 4 obtained by hydrolyzing an aryl ethynyl phthalic acid diester compound as represented by the following Formula 3 is subjected to ring-closing:

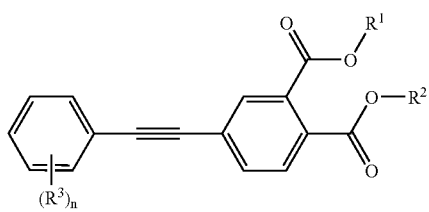

Formula 3

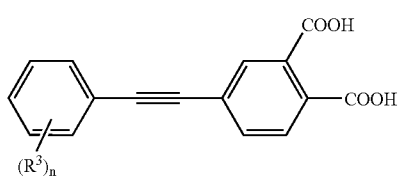

Formula 4

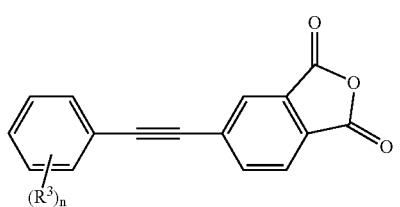

Formula 5 wherein $R^3$ represents a halogen atom, a hydroxyl group, an alkyl group having 1 to 10 carbon atoms, an aryl group having 6 to 10 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms or a perfluoroalkoxy group having 1 to 6 carbon atoms; n represents an integer of from 0 to 5; and when n represents 2 or more, such that $R^3$ is present in plurality, each $R^3$ may be the same as or different from any other $R^3$ or linked thereto to form a ring, and wherein, in Formula 3, $R^1$ and $R^2$ each independently represent an alkyl group having 1 to 8 carbon atoms, a cycloalkyl group or an aryl group.

A fifth aspect of the invention is to provide the method for producing an aryl ethynyl phthalic anhydride represented by Formula 5 in the fourth aspect of the invention, wherein the hydrolysis is alkali hydrolysis in which a reaction mixture obtained by hydrolyzing the aryl ethynyl phthalic acid diester compound represented by Formula 3 is subjected to an adsorbent treatment followed by addition of an acid to obtain an aryl ethynyl phthalic acid compound represented by Formula 4.

A sixth aspect of the invention is to provide the method for producing an aryl ethynyl phthalic anhydride as represented by Formula 5 in the fifth aspect of the invention, wherein the adsorbent treatment is an adsorbent treatment using active carbon.

A seventh aspect of the invention is to provide a fluorine-containing aryl ethynyl phthalic anhydride represented by the following Formula 5A:

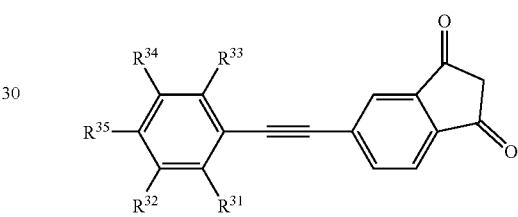

Formula 5A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; and when $R^{31}$, $R^{32}$, $R^{33}$ and $R^{34}$ are hydrogen atoms, $R^{35}$ is a fluorine atom.

An eighth aspect of the invention is to provide a fluorine-containing aryl ethynyl phthalic anhydride as represented by Formula 5A in the seventh aspect of the invention, wherein: (1) when any one of $R^{31}$, $R^{32}$, $R^{33}$, $R^{34}$ and $R^{35}$ is a fluorine atom, the remaining groups are hydrogen atoms; (2) when $R^{31}$ is a trifluoromethyl group, $R^{32}$, $R^{33}$, $R^{34}$ and $R^{35}$ are all hydrogen atoms; or (3) when $R^{32}$ is a trifluoromethyl group, $R^{31}$, $R^{33}$, $R^{34}$ and $R^{35}$ are all hydrogen atoms.

A ninth aspect of the invention is to provide a fluorine-containing aryl ethynyl phthalic acid or salt thereof represented by Formula 4A:

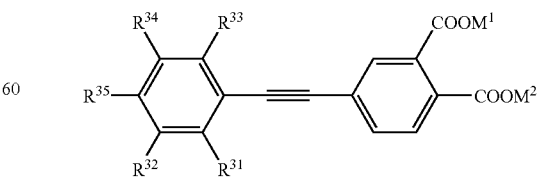

Formula 4A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and $M^1$ and $M^2$ each independently represent a hydrogen atom or a metal atom.

A tenth aspect of the invention is to provide a fluorine-containing aryl ethynyl phthalic acid or salt thereof represented by Formula 4A according to the ninth aspect of the invention, wherein: (1) any one of $R^{31}$, $R^{32}$, $R^{33}$, $R^{34}$ and $R^{35}$ represents a fluorine atom, the remaining groups are hydrogen atoms; (2) when $R^{31}$ represents a trifluoromethyl group, $R^{32}$, $R^{33}$, $R^{34}$ and $R^{35}$ are hydrogen atoms; or (3) when $R^{32}$ represents a trifluoromethyl group, $R^{31}$, $R^{33}$, $R^{34}$ and $R^{35}$ represent hydrogen atoms.

An eleventh aspect of the invention is to provide a method for producing a fluorine-containing aryl ethynyl phthalic anhydride represented by the following Formula 5A obtained by subjecting a fluorine-containing aryl ethynyl phthalic acid or salt thereof represented by the following Formula 4A to ring-closing:

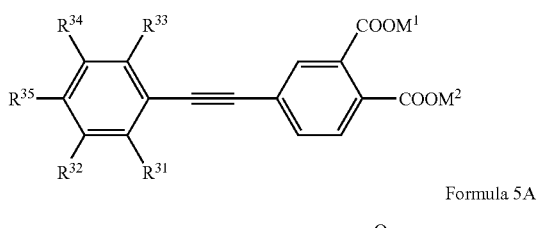

Formula 4A

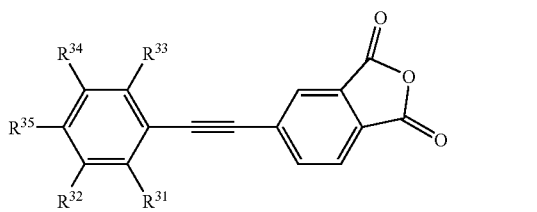

Formula 5A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and $M^1$ and $M^2$ each independently represent a hydrogen atom or a metal atom.

A twelfth aspect of the invention is to provide a method for producing a fluorine-containing aryl ethynyl phthalic acid or a salt thereof represented by the following Formula 4A obtained by the step of subjecting a fluorine-containing aryl ethynyl phthalic acid diester compound represented by the following Formula 3A to hydrolysis:

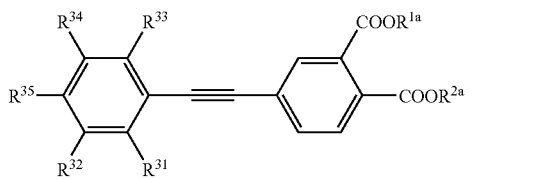

Formula 3A

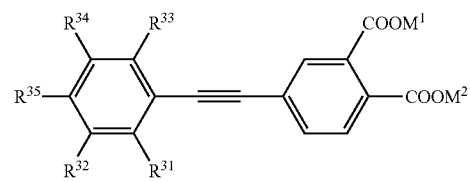

Formula 4A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; $M^1$ and $M^2$ each independently represent a hydrogen atom or a metal atom, and $R^{1a}$ and $R^{2a}$ each independently represent an alkyl group.

A thirteenth aspect of the invention is to provide a method for producing a fluorine-containing aryl ethynyl phthalic anhydride as set forth in the eleventh aspect of the invention, wherein the fluorine-containing aryl ethynyl phthalic anhydride is obtained by using a fluorine-containing aryl ethynyl phthalic acid or a salt thereof represented by Formula 4A obtained by the method according to the twelfth aspect of the present invention.

DETAILED DESCRIPTION OF THE INVENTION

Hereinafter, the present invention will be described in detail.

Firstly, an aryl ethynyl phthalic acid diester compound represented by the following Formula 1 of the present invention is described in detail:

Formula 1 wherein $Q^1$ and $Q^2$ are different from each other and $Q^1$ represents a substituted or unsubstituted aryl group, and $Q^2$ represents a group represented by the following Formula 2:

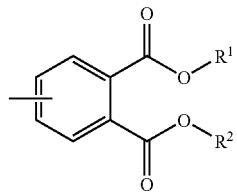

Formula 2 wherein $R^1$ and $R^2$ each independently represent any one of an alkyl group, a cycloalkyl group and an aryl group.

Examples of aryl groups represented by $Q^1$ include a substituted or unsubstituted aromatic hydrocarbon group (preferably having 6 to 12 carbon atoms) and a substituted or unsubstituted aromatic heterocyclic group (preferably having 0 to 12 carbon atoms) and a substituted or unsubstituted aromatic hydrocarbon is preferable. Examples of such aryl groups include a phenyl group, a 1-naphthyl group, a 2-naphthyl group, a 2-anthryl group, a pyridyl group, a furyl group and a thienyl group. Among these groups, a phenyl group, a 1-naphthyl group, a 2-naphthyl group, a 2-anthryl group and a thienyl group are preferable, a phenyl group and a 1-naphthyl group are more preferable, and a phenyl group is most preferable.

Examples of substituents which may be present in an aryl group represented by $Q^1$ include a halogen atom, a hydroxyl group, an alkyl group having 1 to 10 carbon atoms, a cycloalkyl group having 3 to 10 carbon atoms, an aryl group having 6 to 12 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms, a perfluoroalkoxy group having 1 to 6 carbon atoms, and the like. Among these substituents, a fluorine atom, a hydroxyl group, an alkyl group having 1 to 6 carbon atoms, a cycloalkyl group having 3 to 6 carbon atoms, an alkoxy group having 1 to 6 carbon atoms, an aryl group having 6 to 12 carbon atoms, an aryloxy group having 6 to 12 carbon atoms, a perfluoroalkyl group having 1 to 3 carbon atoms, a perfluoroalkoxy group having 1 to 3 carbon atoms are preferred as substituents and, further, an alkyl group having 1 to 4 carbon atoms, an alkoxy group having 1 to 4 carbon atoms, a phenyl group and a phenoxy group are more preferred. These substituents may be present either singly or in plurality and, when plural substituents are present, they may be the same as or different from one another. Further, these substituents may be bonded with one another to form a carbon ring or a heterocycle.

Specific examples of the substituents which may be present in the aryl group as represented by $Q^1$ include a fluorine atom, a hydroxyl group, a methyl group, an ethyl group, a 2-propyl group, a tert-butyl group, a 1-octyl group, a tert-octyl group, a cyclohexyl group, a cyclopentyl group, a cyclopropyl group, a 2-ethylhexyl group, a methoxy group, an ethoxy group, a 2-propoxy group, a tert-butoxy group, a 1-hexyloxy group, a cyclohexyloxy group, a 1-octyloxy group, a 1-naphthyl group, a 2-naphthyl group, a phenyl group, an azulenyl group, a 1-naphthoxy group, a 2-naphthoxy group, a phenoxy group, a pentafluorophenyl group, a 1-pentafluoropropyl group, a trifluoromethyl group, a 1-pentafluoropropoxy group, a trifluoromethoxy group and a pentafluorophenoxy group. Among these substituents, a fluorine atom, a hydroxyl group, an ethyl group, a 2-propyl group, a tert-butyl group, a cyclopropyl group, a cyclohexyl group, a methoxy group, an ethoxy group, a 2-propoxy group, a tert-butoxy group, a cyclohexyloxy group, a 1-naphthyl group, a 2-naphthyl group, a phenyl group, a 1-naphthoxy group, a 2-naphthoxy group, a phenoxy group and trifluoromethoxy group are preferred, and a fluorine atom, a trifluoromethyl group, a tert-butoxy group, a phenyl group and a phenoxy group are more preferred.

In Formula 2, $R^1$ and $R^2$ each independently represent an alkyl group, a cycloalkyl group or an aryl group and, preferably, an alkyl group having 1 to 8 carbon atoms, a cycloalkyl group having 3 to 8 carbon atoms and an aryl group having 6 to 12 carbon atoms and, more preferably, an alkyl group having 1 to 6 carbon atoms, a cycloalkyl group having 3 to 6 carbon atoms and an aryl group having 6 to 10 carbon atoms. Specific examples of $R^1$ and $R^2$ include a methyl group, an ethyl group, a 2-propyl group, a 1-butyl group, a 1-octyl group, a tert-butyl group, a cyclohexyl group, a cyclopentyl group, a cyclopropyl group, a 2-ethylhexyl group, a 1-naphthyl group, a 2-naphthyl group, a phenyl group, a 4-toluyl group and a 2-toluyl group. Particularly, a methyl group, an ethyl group, a 2-propyl group, a tert-butyl group and a phenyl group are preferred and a methyl group and an ethyl group are more preferred.

Among aryl ethynyl phthalic acid diester compounds represented by Formula 1, more preferable compounds can be represented by the following Formula 3:

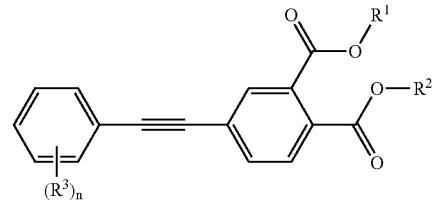

Formula 3 wherein $R^1$ and $R^2$ are the same as $R^1$ and $R^2$ as described in Formula 2, respectively, and preferable ranges and specific examples of $R^1$ and $R^2$ are also the same as those of $R^1$ and $R^2$ as described in Formula 2, respectively;

$R^3$ is the same as any one of those described as substituents which may be present in the aryl group represented by $Q^1$ in Formula 1 and the preferable range of $R^3$ is also the same as for these substituents. Preferable examples of $R^3$ include a fluorine atom, a trifluoromethyl group, a tert-butyl group, a tert-butoxy group, a phenyl group, a phenoxy group and a cyano group; n represents an integer of from 0 to 5 and, when n is 2 or more, such that $R^3$ is present in plurality, each $R^3$ may be the same as or different from any other $R^3$ and, further, each $R^3$ may be linked to one another to form a ring (preferably, a carbon ring or a heterocycle). The preferable range of n is from 0 to 2 and, more preferably, 0 or 1.

Hereinafter, specific examples of aryl ethynyl phthalic acid diester compounds according to the invention will be described, but the invention is not limited thereto.

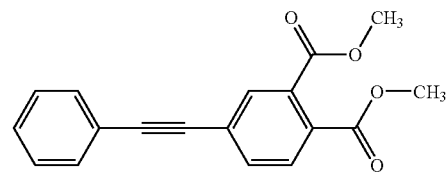

No. 1

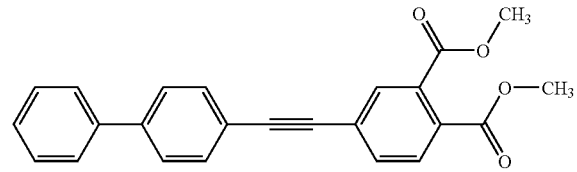

No. 2

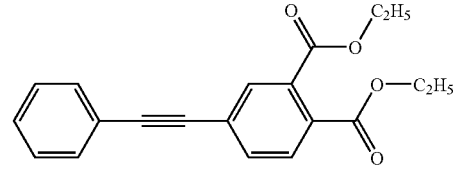

No. 3

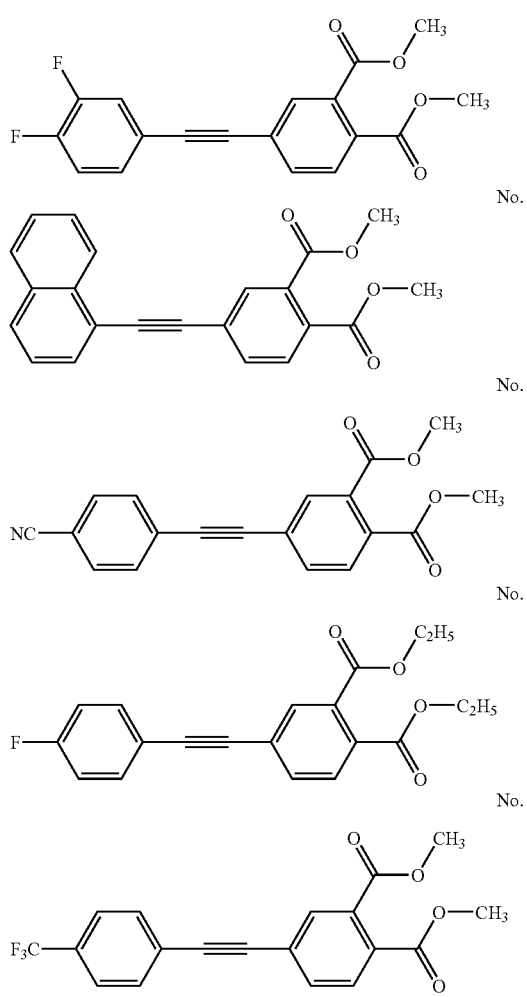

The aryl ethynyl phthalic acid diester compound as represented by Formula 1 can be synthesized by, for example, a method in which a substituted or unsubstituted aryl acetylene compound and a phthalic acid diester having a halogen substituent are coupled in a basic condition by using a palladium (II) complex having copper iodide and a phosphine ligand as a catalyst. According to this method, the aryl ethynyl phthalic acid diester compound as represented by Formula 1 according to the invention can be synthesized in high yield, such that the method is a preferable method. Further, reference may be made to synthetic methods as described in, for example, Journal of Organic Chemistry, vol. 48, pp. 5135 to 5137, 1983 and JP-A No. 10-114691.

Examples of methods for isolating the aryl ethynyl phthalic acid diester compound according to the invention from a reaction mixture include a separation-purification method in which an extraction process is carried out with an organic solvent, followed by chromatography, crystallization, recrystallization or the like. Since the aryl ethynyl phthalic acid diester compound according to the invention has excellent crystallinity, isolation by crystallization is preferred. In a case in which the aryl ethynyl phthalic acid diester compound is crystallized by cooling a solution extracted by the organic solvent, the aryl ethynyl phthalic acid diester compound can be isolated with an ordinary solid-liquid separation. It is also possible that the aryl ethynyl phthalic acid diester compound is crystallized out of a suitable solvent system and, then, isolated by ordinary solid-liquid separation.

Examples of such organic solvents for extracting the aryl ethynyl phthalic acid diester compounds include ether type solvents such as diethyl ether, diisopropyl ether, methyl t-butyl ether and methoxy benzene; ester type solvents such as ethyl acetate and n-butyl acetate; aliphatic hydrocarbon solvents as represented by hexane and heptane; and aromatic hydrocarbon solvents. From the standpoint of applicability to an industrial large-scale production, availability and the like, the ester type solvents, the aliphatic hydrocarbon solvents and the aromatic hydrocarbon solvents are preferred. Examples of organic solvents to be preferably used include toluene, xylene (any one of o-, m- or p-type and mixtures thereof in any mixture ratios are permissible), mesitylene, ethyl benzene, isopropyl benzene (cumene), chlorobenzene, hexane, heptane, ethyl acetate and n-butyl acetate. Among these solvents, toluene, xylene, ethyl benzene, hexane, heptane, ethyl acetate and n-butyl acetate are more favorable and toluene, hexane, heptane and ethyl acetate are still more favorable.

Examples of solvent systems for crystallizing the aryl ethynyl phthalic acid diester compound include a mixed system comprising any one of the above-described organic solvents and any one other organic solvent. Examples of other organic solvents include lower alcohols each having 1 to 4 carbon atoms, acetonitrile and propionitrile. Among these solvents, a solvent to be preferably used can be selected from those lower alcohols having 1 to 4 carbon atoms and acetonitrile. More preferable solvents are methanol, 2-propanol and acetonitrile. Examples of preferable solvents for crystallization include toluene alone, hexane alone, a mixed system of toluene and 2-propanol, a mixed system of hexane and 2-propanol, a mixed system of heptane and 2-propanol, and a mixed system of hexane and acetonitrile. By using any one of the above-described methods, impurities and coloring components attributable to the reaction processes can effectively be removed and, accordingly, the aryl ethynyl phthalic acid diester compound with high purity can be obtained.

Next, a method for producing the aryl ethynyl phthalic acid anhydride according to the invention will be described.

A production method according to the invention is a method in which the aryl ethynyl phthalic acid diester represented by Formula 3 is converted into an aryl ethynyl phthalic acid compound represented by Formula 4 by hydrolysis and, then, the aryl ethynyl phthalic acid compound is subjected to a ring closing reaction to produce an aryl ethynyl phthalic anhydride represented by Formula 5.

As methods of hydrolyzing ester compounds according to the invention, an alkali hydrolysis is preferable. As bases to be used for such alkali hydrolysis, an alkali metal hydroxide, an alkali earth metal hydroxide, an alkali metal alkoxide and an organic salt can be used. A preferable base is an alkali metal hydroxide. Examples of such alkali metal hydroxides include sodium hydroxide, potassium hydroxide, lithium hydroxide and cesium hydroxide. Sodium hydroxide or potassium hydroxide are preferably used. These alkali metal hydroxides may each be used in flake or pellet form or in a solution having an arbitrary concentration (for example, a 25% by mass of aqueous sodium hydroxide solution or a 48% by mass aqueous potassium hydroxide solution). Taking into account industrial scale production, it is convenient to use the bases in a solution state. An amount of the alkali metal hydroxide to be used in a hydrolysis step is preferably in the range of from 2.0 to 10 times by mole, relative to the aryl ethynyl phthalic acid diester compound represented by Formula 3, more preferably in the range of from 2.0 to 5.0 times by mole and, still more preferably, in the range of from 2.1 to 3.0 times by mole.

Reaction solvents which can be used in the hydrolysis step are not particularly limited as long as they do not cause an operational problem, do not hinder a reaction and do not give rise to an adverse effect on the reaction due to decomposition in the hydrolysis step in the present invention. However, a mixed system of water and an organic solvent is preferably selected. Preferable examples of organic solvents which can be used in combination with water include alcohol type solvents such as methanol, ethanol and 2-propanol; non-proton type polar solvents such as N-methyl pyrrolidone, sulfolane and N,N-dimethyl imidazolidinone; ether type solvents such as 1,2-dimethoxyethane and tetrhydroxy furan; and nitrogen-containing heteroaromatic type solvents such as pyridine. Further, a plurality of solvents selected from the above-described solvents can be used in combination. Among these solvents, alcohol type solvents, non-proton type polar solvents and pyridine are preferred and methanol, ethanol, 2-propanol, N-methyl pyrrolidone, sulfolane and N,N-dimethyl imidazolidinone are more preferably used. The most preferable solvent is water, methanol, ethanol, N-methyl pyrrolidone or sulfolane, or a mixed system of water and one, two or three types of solvents selected from these solvents.

Reaction temperature in the hydrolysis step is preferably in the range of from 0 to 200° C., more preferably in the range of from 20 to 100° C. and, still more preferably, in the range of from 20 to 60° C. Although reaction time period varies according to loading amount and reaction temperature, it is preferably in the range of from 0.5 to 12 hours and, more preferably, in the range of from 1 to 6 hours. As the reaction proceeds, the aryl ethynyl phthalic acid diester compound represented in Formula 3 of the invention is dissolved. In the hydrolysis step, an inert atmosphere is not necessarily required; however, the reaction may be performed in a flow of an argon gas or a nitrogen gas.

An after-treatment of a reaction mixture after completion of the hydrolysis is preferably performed by a method of adsorbent treatment. Examples of such adsorbents include silica gel, magnesium oxide, aluminum oxide, and a commercially available adsorbent comprising a mixed system of these metal oxides, active carbon, zeolite and clay mineral such as montmorillonite. Among these adsorbents, silica gel, a commercially available adsorbent comprising a mixed system of metal oxides, or active carbon is preferable, and a plurality of these adsorbents can be used in combination. In the present invention, the most preferable adsorbent is active carbon. The amount of the adsorbent to be used is preferably in the range of from 0.1 to 200% by mass, relative to the mass of the aryl ethynyl phthalic acid diester compound used as a starting material, more preferably in the range of from 0.5 to 50% by mass and, still more preferably, in the range of from 1 to 20% by mass. The temperature of the adsorbent treatment is, preferably, in the range of from 0 to 80° C., more preferably in the range of from 10 to 60° C. and, still more preferably, in the range of from 20 to 40° C. Although the time period of the adsorbent treatment varies with the loading amount and the temperature, it is preferably in the range of from 0.5 to 12 hours. Further, it is also possible that the reaction mixture in the step of the adsorbent treatment is allowed to stand overnight. The adsorbent after use can easily be removed by ordinary solid-liquid separation. In this process, a filter aid such as Celite, radiolite, cellulose powder and the like may be used.

In the present invention, it is particularly preferable that the adsorbent treatment is performed, followed by converting a salt of the aryl ethynyl phthalic acid into the acid thereof by adding an acid to form the aryl ethynyl phthalic acid represented by Formula 4. Such conversion from the salt of the aryl ethynyl phthalic acid present in the reaction mixture into the salt thereof to form the aryl ethynyl phthalic acid compound as represented by Formula 4 is preferably carried out by allowing an acid to act on a reaction solution after the adsorbent treatment. An amount of the acid to be used is preferably one equivalent or more and, more preferably, 1 to 1.5 equivalents, relative to one carboxylic group. As types of such acids, acids having a pK value of 4 or less are preferable, more preferably 2.5 or less. These acids include an organic acid such as organic sulfonic acids, for example, methane sulfonic acid, carboxylic acids, for example, formic acid, acetic acid, trichloroacetic acid and citric acid or mineral acids which are inorganic acids such as hydrohalogenic acid, sulfuric acid, nitric acid, phosphoric acid and the like. Of these acids, mineral acids are preferable. Specifically, hydrochloric acid, sulfuric acid, methane sulfonic acid, acetic acid, citric acid and formic acid are preferable. Among these acids, hydrochloric acid, sulfuric acid and methane sulfonic acid are preferable, and hydrochloric acid, sulfuric acid are more preferable. The aryl ethynyl phthalic acid compound represented by Formula 4 is precipitated by carrying out such conversion from the salt to the acid, and a targeted substance can be isolated by performing ordinary solid-liquid separation.

At the time of the conversion into the aryl ethynyl phthalic acid compound as represented by Formula 4 by performing the conversion of the salt to the acid, an organic solvent which can be phase-separated from water in a two layer manner may coexist. This is one of the preferred embodiments according to the present invention. Examples of such solvents which can be phase-separated from water in a two layer manner include ether type solvents such as diethyl ether, diisopropyl ether, methyl t-butyl ether, methoxy benzene and ethoxybenzene; ester type solvents such as ethyl acetate and n-butyl acetate; aliphatic hydrocarbon solvents typically represented by hexane and heptane; and aromatic hydrocarbon solvents. Examples of organic solvents, which are favorably used from the standpoint of applicability to industrial large-scale production, availability and the like, include methyl t-butyl ether, toluene, xylene (any one of o-, m- or p-type and mixtures thereof in any mixture ratios are permissible), mesitylene, ethyl benzene, t-butyl benzene, isopropyl benzene (cumene), chlorobenzene, ethyl acetate, n-propyl acetate and n-butyl acetate. Among these solvents, methyl t-butyl ether, toluene, xylene, ethyl benzene, ethyl acetate, n-butyl acetate are more favorable and methyl t-butyl ether, toluene, xylene and ethyl acetate are still more preferable. A plurality of these solvents can be used in combination. The organic solvent is allowed to coexist with water, so that the aryl ethynyl phthalic acid compound which is prepared by converting the salt into the acid can effectively be extracted in an organic layer. On the other hand, an inorganic salt and the like are transferred into a water layer and removed. The organic layer containing the aryl ethynyl phthalic acid compound separated from the reaction mixture separated into two layers as such can be allowed to proceed to the subsequent ring-closing step. This is industrially advantageous.

A method in which the aryl ethynyl phthalic acid compound as represented by Formula 4 is subjected to ring closing, preferably, chemical or thermal ring closing to derive an aryl ethynyl phthalic anhydride as represented by Formula 5 is not particularly limited. For example, the ring closing step can easily be performed by heating together with acetic anhydride in the presence of a solvent. Alternatively, the ring closing process can be performed by heating at about 110° C. to about 150° C. In this case, it is preferable to use a solvent such as toluene having a property capable of removing water from an azeotrope.

Hereinafter, the ring closing method will be described in detail.

A reaction agent is used for performing the ring-closing chemically. The reaction agents include acetic anhydride, succinic anhydride, acetyl chloride, chlorosulfonic acid, thionyl chloride, phosphorus oxychloride and propenyl acetate. Among these reaction agents, acetic anhydride, acetyl chloride, chlorosulfonic acid and phosphorus oxychloride are preferable, and acetic anhydride and phosphorus oxychloride are more preferable.

The reaction solvents are not specifically limited to specific solvents as long as the solvents do not react with an acid anhydride to form an ester or acid amide, such as an alcohol or amine. Examples of such solvents include hydrocarbon-based solvents (including aromatic solvents and aliphatic solvents), halogen-based solvents (including aromatic solvents and aliphatic solvents) amide-based solvents, ester-based solvents, ketone-based solvents, nitril-based solvents, and ether-based solvents. Among these solvents, aromatic hydrocarbon-based solvents, ester-based solvents, ketone-based solvents, nitril-based solvents and ether-based solvents are preferable, and aromatic hydrocarbon-based solvents, ester-based solvents, ketone-based solvents are more preferable.

Specific examples of the solvents include decane, toluene, xylene, chlorobenzene, dimethyl acetoamide, dimethyl formamide, N-methyl-2-pyrrolidone, ethylacetate, butylacetate, diethyl carbonate, cyclohexanone, methyl isobutyl ketone, methyl ethylketone, acetone, acetonitril, propionitril, anisole, t-butyl methylether, diisopropyl ether, and the like. Among these solvents, toluene, xylene, ethylacetate, butylacetate, diethyl carbonate, cyclohexanone, methyl isobutyl ketone, methyl ethylketone, acetone, acetonitril, propionitril, anisole and t-butyl methylether, diisopropyl ether are preferable, and toluene, xylene, ethylacetate, butylacetate, diethyl carbonate, cyclohexanone, methyl isobutyl ketone, methyl ethylketone and acetone are more preferable.

On the other hand, examples of methods of performing ring-closing include a method of utilizing sublimation without a solvent, and a method of using a solvent which has an azeotropic property with water to remove water formed when a ring is closed. Of these, the method using the solvent which has an azeotropic property with water is preferable.

Examples of these solvents include hydrocarbon-based solvents (including aromatic solvents and aliphatic solvents), halogen-based solvents (including aromatic solvents and aliphatic solvents), ester-based solvents, ketone-based solvents and ether-based solvents. Among these solvents, aromatic hydrocarbon-based solvents, ester-based solvents, and ether-based solvents are preferable, and aromatic hydrocarbon-based solvents and ester-based solvents are more preferable.

Specific examples include decane, toluene, xylene, chlorobenzene, butylacetate, diethyl carbonate, cyclohexanone, methyl isobutyl ketone, anisole, 1,2-dimethoxyethane, and the like. Among these solvents, toluene, xylene, butylacetate, diethyl carbonate, anisole, 1,2-dimethoxyethane are preferable, and toluene, xylene, chlorobenzene, butylacetate and diethyl carbonate are more preferable.

In many cases, since an aryl ethynyl phthalic anhydride as represented by Formula 5 is precipitated as a crystal by cooling the reaction solution after the reaction is complete, a targeted substance can be isolated by performing an ordinary solid-liquid separation, or, a poor solvent may be use in combination. The aryl ethynyl phthalic anhydride to be obtained by such method as described above is highly pure and can favorably be used as a terminal end-blocking agent for, for example, a polyimide resin.

Specific examples of such aryl ethynyl phthalic anhydrides to be favorably produced by the production method according to the invention are as follows; however, the invention is not limited thereto:

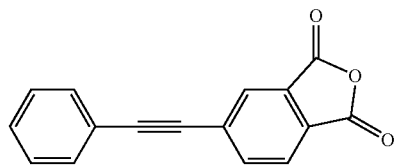

No. 10

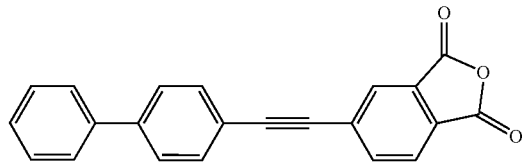

No. 11

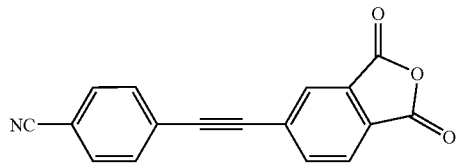

No. 12

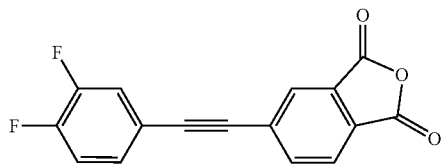

No. 13

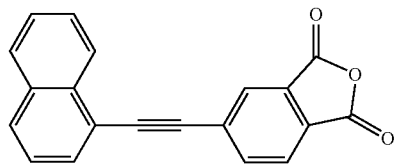

No. 14

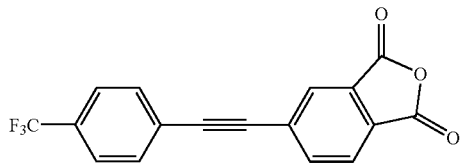

No. 15

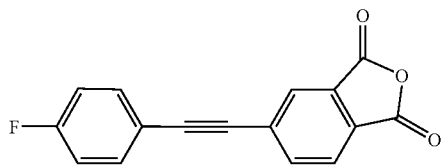

No. 16

-continued

No. 17

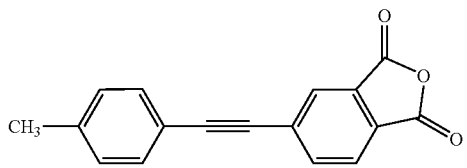

In aryl ethynyl phthalic anhydrides represented by Formula 5 above, a fluorine-containing aryl ethynyl phthalic anhydride represented by the following Formula 5A can reduce a hygroscopicity of a polyimide when the fluorine-containing aryl ethynyl phthalic anhydride is used as a terminal-end blocking agent for the polyimide. Further, since the fluorine-containing aryl ethynyl phthalic anhydride can change a temperature range and a temperature width for the thermal curing due to reaction of an ethynyl group, it is preferable.

Next, a fluorine-containing aryl ethynyl phthalic anhydride represented by the following Formula 5A will be described.

Formula 5A

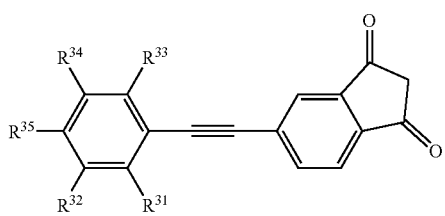

wherein (1) $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; and when $R^{31}$, $R^{32}$, $R^{33}$ and $R^{34}$ are hydrogen atoms, $R^{35}$ is a fluorine atom.

In Formula 5A, the number of hydrogen atoms as $R^{31}$, $R^{32}$, $R^{33}$, $R^{34}$ and $R^{35}$ is preferably 1 to 4, more preferably 2 to 4, further more preferably 3 to 4, and most preferably 4. In Formula 5A, the number of fluorine atoms as $R^{31}$, $R^{32}$, $R^{33}$, $R^{34}$ and $R^{35}$ is preferably 1 to 4, more preferably 1 to 3, further more preferably 1 to 2, and most preferably 1.

In Formula 5A, while all of $R^{31}$, $R^{32}$, $R^{33}$, $R^{34}$ and $R^{35}$ may be trifluoromethyl groups, the number of trifluoromethyl groups is preferably 1 to 3, more preferably 1 to 2, and most preferably 1. Fluorine atom(s) and trifluoromethyl group(s) may coexist in the groups of $R^{31}$, $R^{32}$, $R^{33}$, $R^{34}$ and $R^{35}$ in Formula 5A.

In Formula 5A, preferable compounds are: (1) any one of $R^{31}$, $R^{32}$, $R^{33}$, $R^{34}$ and $R^{35}$ is a fluorine atom and the remaining are all hydrogen atoms; (2) $R^{31}$ represents a trifluoromethyl group and the remaining are all hydrogen atoms; and (3) $R^{32}$ represents a trifluoromethyl group and all of $R^{31}$, $R^{33}$, $R^{34}$ and $R^{35}$ represent hydrogen atoms. In the present invention, it is preferable that $R^{31}$, $R^{32}$, $R^{33}$, $R^{34}$ and $R^{35}$ are selected from hydrogen atoms and fluorine atoms; namely, the above (1) is preferable.

Specifically, the compounds represented by Formula 5A preferably include the following compounds:

No. 16

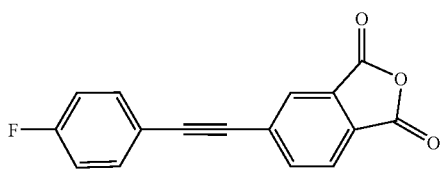

No. 18

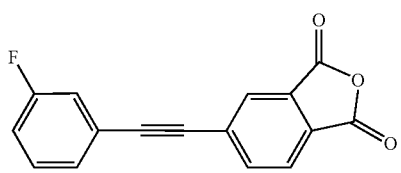

No. 19

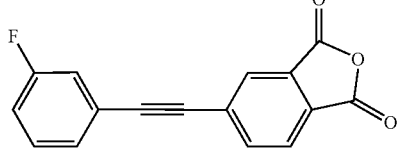

No. 20

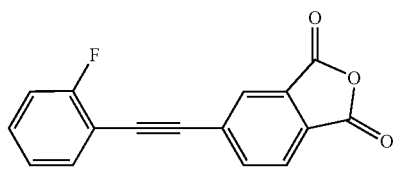

No. 21

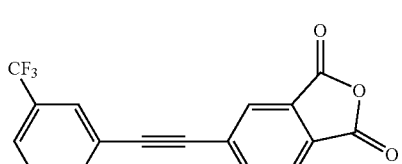

Among the above compounds, the compounds represented by Nos. 16 and 18 are most preferable.

The fluorine-containing aryl ethynyl phthalic anhydride represented by Formula 5A is synthesized by subjecting the fluorine-containing aryl ethynyl phthalic acid or a salt thereof represented by Formula 4A to ring closing. The method which has been described in the above in the method of subjecting the compound represented by Formula 4 to ring closing to form the compound represented by Formula 5 is applicable to the method of subjecting the fluorine-containing aryl ethynyl phthalic acid or a salt thereof represented by Formula 4A to ring closing.

Formula 4A

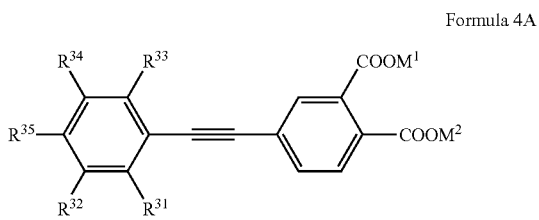

wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and preferable combinations of groups represented by $R^{31}$, $R^{32}$, $R^{33}$, $R^{34}$ and $R^{35}$ are the same as those in Formula 5A. $M^1$ and $M^2$ each independently represent a hydrogen atom or a metal atom. Metal atoms represented by $M^1$ and $M^2$ are preferably an alkali metal atom and an alkali earth metal atom, more preferably an alkali metal atom. In this case, a single alkali earth metal atom can be used in place of two monovalent metal atoms represented by $M^1$ and $M^2$.

More specifically, groups represented by $M^1$ and $M^2$ are a hydrogen atom, sodium or potassium. Preferably, groups represented by $M^1$ and $M^2$ are the same, and the groups are selected from a hydrogen atom, sodium and potassium, more preferably, $M^1$ and $M^2$ are selected from a hydrogen atom and sodium, and most preferably, $M^1$ and $M^2$ are both hydrogen atoms.

In the present invention, the following compounds are preferably used:

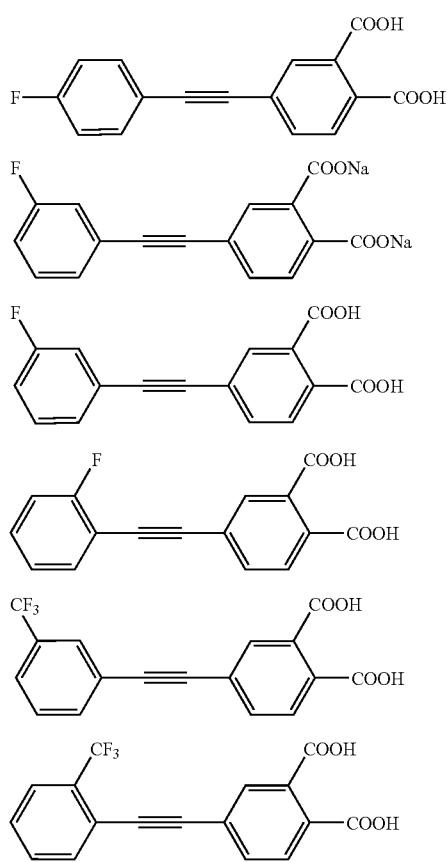

Among these compounds, the compounds Nos. 22, 23 and 24 are preferable.

The fluorine-containing aryl ethynyl phthalic acid or salt thereof may be synthesized by any method.

In the present invention, the fluorine-containing aryl ethynyl phthalic acid or salt thereof are preferably synthesized by subjecting the compounds represented by the above Formula 3, more specifically, the fluorine-containing aryl ethynyl phthalic acid diester represented by the following Formula 3A to hydrolysis. The hydrolyzing method which is described in the method of synthesizing the compound represented by Formula 4 from the compound represented by Formula 3 is applicable to this hydrolysis.

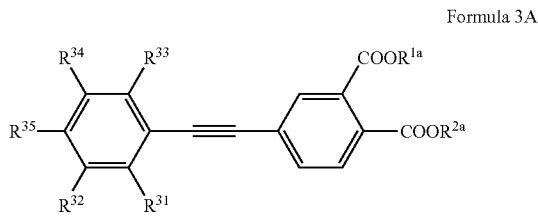

Formula 3A wherein $R^{31}$, $R^{32}$, $R^{33}$, $R^{34}$ and $R^{35}$ each independently represent a hydrogen atom, a fluorine atom or a trifluoromethyl group; wherein $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; $R^{1a}$ and $R^{2a}$ each independently represent an alkyl group; preferable combinations of groups represented by $R^{31}$, $R^{32}$, $R^{33}$, $R^{34}$ and $R^{35}$ are the same as those in Formula 5A; and alkyl groups represented by $R^{1a}$ and $R^{2a}$ are preferably alkyl groups having 1 to 8 carbon atoms. Preferred examples of the alkyl groups include a methyl group, ethyl group and t-butyl group, and a methyl group and ethyl group are more preferable. Specific examples include dimethyl esters and diethyl esters corresponding to the compound Nos. 16, 18 to 21.

In the present invention, it is most preferable that the fluorine-containing aryl ethynyl phthalic anhydride represented by Formula 5A is produced in such a manner that the compound represented by Formula 3A is hydrolyzed to form the fluorine-containing aryl ethynyl phthalic acid or salt thereof represented by Formula 4A, followed by subjecting the resultant fluorine-containing aryl ethynyl phthalic acid or salt thereof, to ring-closing.

The method of synthesizing the fluorine-containing aryl ethynyl phthalic acid or salt thereof represented by Formula 4A is basically the same as that of synthesizing the fluorine-containing aryl ethynyl phthalic acid or salt thereof represented by Formula 4, but in the case of the salt of the fluorine-containing aryl ethynyl phthalic acid (where M1 and M2 are metal atoms), the objective compound is preferably taken out of the system by the following method.

The fluorine-containing aryl ethynyl phthalic acid salt is precipitated by removing a solvent from the reaction system by reducing pressure, or precipitated by adding an electrolyte or a water-soluble organic solvent to the reaction system, and can be taken out from the system by a solid-liquid separation method generally used. Among these methods, the precipitation by adding an electrolyte or a water-soluble organic solvent is preferable. More preferably, the fluorine-containing aryl ethynyl phthalic acid salt formed by the reaction is taken out from the system by adding a water-soluble organic solvent.

Examples of the electrolyte or water-soluble organic solvent to be added to precipitate the fluorine-containing aryl ethynyl phthalic acid salt of the present invention includes sodium chloride or an aqueous solution thereof, potassium chloride or an aqueous solution thereof, calcium chloride or an aqueous solution thereof, methanol, ethanol, isopropyl alcohol, dimethylacetamide, dimethylformamide, acetonitrile, terahydrofuran, acetone, ethylene glycol, glycerin and the like. Among these solvents, methanol, ethanol, isopropyl alcohol, acetonitrile, terahydrofuran, acetone and ethylene glycol are preferable, and methanol, ethanol, isopropyl alcohol and acetone are more preferable.

The fluorine-containing aryl ethynyl phthalic acid represented by Formula 4A (where $M^1$ and $M^2$ are each a hydrogen atom) is preferably obtained by converting the fluorine-containing aryl ethynyl phthalic acid salt (where $M^1$ and $M^2$ are each a metal atom) to the corresponding acid. More specifically, the fluorine-containing aryl ethynyl phthalic acid can be obtained by adding an acid to the crystal or solution of the salt of the fluorine-containing aryl ethynyl phthalic acid obtained by the manner above as a starting material, and the description and preferable method relating to the fluorine-containing aryl ethynyl phthalic acid represented by Formula 4 above is applicable to the fluorine-containing aryl ethynyl phthalic acid represented by Formula 4A.

The method and preferable method of synthesizing the fluorine-containing aryl ethynyl phthalic anhydride represented by Formula 5 from the fluorine-containing aryl ethynyl phthalic acid compound represented by Formula 4 above is applicable to the method of synthesizing the fluorine-containing aryl ethynyl phthalic anhydride represented by Formula 5A from the fluorine-containing aryl ethynyl phthalic acid thus obtained.

EXAMPLES

Hereinafter, the present invention will be described in detail with reference to examples and comparative examples; however, the invention is not limited thereto.

Example 1

Compound No. 1: Synthesis of 4-phenyl ethynyl dimethyl phthalate

Under a nitrogen gas stream, 24.6 g of 4-bromo-dimethyl phthalate, 11.03 g of ethynyl benzene, 71 mg of triphenylphosphine, 20 mg of trans-dichloro-bis (triphenylphosphine)palladium (II) and 171 mg of cuprous iodide were placed in a three-necked flask of 300-ml capacity and, then, 60 ml of triethylamine was poured therein while stirring. The reaction mixture was refluxed for 12 hours while heating at 100° C., cooled to room temperature and, thereafter, the resultant reaction solution was filtered to remove formed salts and catalysts and, then, washed with 60 ml of toluene. The filtrate and a rinsing solution were combined and concentrated, to obtain 25.1 g of a crude crystal of 4-phenyl ethynyl diethyl phthalate.

The thus-obtained crude crystal was recrystallized from a mixed system comprising 2-propanol/n-hexane (50 ml/100 ml), to thereby obtain 22.9 g of 4-phenyl ethynyl diethyl phthalate. The yield thereof was 86.4%.

$^1$H-NMR (CDCl$_3$): 3.92 ppm (s, 3H), 3.93 ppm (s, 3H), 7.36 to 7.39 ppm (m, 3H), 7.52 to 7.56 ppm (m, 2H), 7.66 ppm (q, 1H), 7.75 ppm (d, 1H), 7.85 ppm (d, 1H) IR vmax (KBr): 1269 (s), 1604 (m), 1724 (s), 2210 (w), 2950 (w), 3003 (w) cm$^{-1}$ MS: m+/z=295 Melting point: 76.9° C. to 77.4° C.

Example 2

Compound No. 4: (Synthesis of 4-(3,4-difluorophenyl-ethynyl)dimethyl phthalate)

A crystal of 4-(3,4-difluorophenyl ethynyl)dimethyl phthalate was obtained in generally the same manner as in Example 1 except for using 11.9 g of 3,4-difluoroethynyl benzene in place of ethynyl benzene. The yield thereof was 68.6%. MS: m+/z=331 and melting point was 96.0° C. to 96.7° C.

Example 3

Compound No. 10: Synthesis of 4-phenyl ethynyl phthalic anhydride 10 by Using 4-phenyl ethynyl dimethyl phthalate (Straight Method without Isolation of Dicarboxylic Acid 4-phenyl ethynyl dimethyl phthalate (33.6 g) was suspended in a mixed medium comprising water and methanol and a 25% by mass aqueous solution of sodium hydroxide (40 g) was dropwise added thereto with stirring. The resultant reaction mixture was stirred at 60° C. for 3 hours and, then, after confirming the completion of the reaction, cooled to the inside temperature of 30° C. Thereafter, 1 g of active carbon was added thereto, and, then, stirred for 30 minutes maintaining the same temperature. The resultant mixture was filtered to remove the active carbon, and rinsed with water. The filtrate and a rinsing solution were combined and, then, toluene and ethyl acetate were added to the resultant mixture. Concentrated hydrochloric acid (28 g) was dropwise added to the resultant 2-layered reaction mixture. The mixture was stirred for 30 minutes at room temperature and was allowed to stand, so that an organic layer containing 4-phenyl ethynyl phthalic acid was separated. After partially concentrating the organic layer, acetic anhydride (17 g) was added thereto, and the reaction mixture was refluxed with heating for 4 hours. After the reaction was completed, the resultant reaction mixture was cooled, so that 4-phenyl ethynyl phthalic anhydride was precipitated as a crystal. The crystal was filtered, rinsed and dried, to thereby obtain 26.6 g of 4-phenyl ethynyl phthalic anhydride as a pale yellow crystal. The yield was 94% on the basis of 4-phenyl ethynyl dimethyl phthalate. Physical properties of the substance thus obtained were as follows:

Melting point: 152.1 to 152.3° C.; IR vmax (KBr): 3070 (w), 2200 (m), 1775 (w), 1770 (s), 1755 (vs), 1620 (s), 1495 (m), 1340 (m), 1240 (vs), 940 (m), 900 (vs) cm$^{-1}$;

Turbidity: 0.1 ppm (100 mg of sample/25 mL of ethyl acetate solution);

Visible light absorption: 0.015 (400 nm), 0.004 (450 nm) (100 mg of sample/25 mL of ethyl acetate solution); and GC purity: 99.9% or more (GC measurement conditions: column: DB-5MS, 0.53 mm×30 m; carrier gas: helium, 70 kPa; detection: FID; column temperature: 100° C. to 300° C. (temperature being raised at a rate of 10° C./min).

Example 4

Compound No. 10: Synthesis of 4-phenyl ethynyl phthalic anhydride 10 by Using 4-phenyl ethynyl dimethyl phthalate (a Method of Isolating Dicarboxylic Acid)

4-phenyl ethynyl dimethyl phthalate (33.6 g) was suspended in a mixed medium comprising water and methanol and an aqueous 25% by mass sodium hydroxide solution (40 g) was dropwise added to the mixture while being stirred. The resultant reaction mixture was stirred at 60° C. for 3 hours and, after confirming the completion of the reaction, cooled to the inside temperature of 30° C. Thereafter, 1 g of active carbon was added thereto, stirred for 30 minutes maintaining the same temperature. The resultant mixture was filtered to remove active carbon and, then, washed with water. The filtrate and a washing solution were combined and, concentrated, hydrochloric acid (28 g) was dropwise added to the resultant mixture. After the resultant reaction mixture was stirred for 30 minutes at room temperature, a precipitated crystal was collected by filtration and, then, the thus-collected crystal was rinsed and dried, to thereby obtain 4-phenyl ethynyl phthalic acid as a colorless crystal (melting point: 211.0 to 211.6° C.).

An entire amount of the thus-obtained crystal was suspended in toluene and, acetic anhydride (17 g) was added thereto. The resultant reaction mixture was refluxed with heating for 4 hours. After the reaction was completed, the resultant reaction mixture was cooled, so that 4-phenyl ethynyl phthalic anhydride was precipitated as a crystal. The crystal was filtered, rinsed and dried, to thereby obtain 26.3 g of 4-phenyl ethynyl phthalic anhydride as a pale yellow crystal. The yield was 93% on the basis of 4-phenyl ethynyl dimethyl phthalate. Physical properties of the substance thus obtained were as follows:

Melting point: 152.1 to 152.2° C.; IR: coincided with those in Example 3;

Turbidity: 0.1 ppm (conditions were set to be same as those in Example 3);

Visible light absorption: 0.015 (400 nm), 0.003 (450 nm) (conditions were the same as those in Example 3); and GC purity: 99.9% or more (measurement conditions were the same as those in Example 3).

Comparative Example 1

Compound No. 10: Synthesis of: 4-phenyl ethynyl phthalic anhydride 10 by Using the Method as Described in the Above-Described Patent Document No. 3 (JP-A No. 2003-73372)

In accordance with the method as described in Patent Document No. 3, 4-phenyl ethynyl phthalic anhydride was synthesized from 4-bromophthalic anhydride and phenyl acetylene. The resultant 4-phenyl ethynyl phthalic anhydride was yellowish brown crystalline powder. The yield thereof was 79.1%.

Physical properties were as follows (measurement conditions were the same as those in Example 3):

Melting point: 149.1 to 149.8° C.;

Turbidity: 8.1 ppm;

Visible light absorption: 0.058 (400 nm), 0.015 (450 nm); and

GC purity: 97.5%.

Comparative Example 2

Synthesis of 4-phenyl ethynyl phthalic anhydride by Using the Method as Described in the Above-Described Patent Document No. 2

In accordance with the method as described in Example 1 of Patent Document No. 2 (JP-A No. 11-180970), 4-phenyl ethynyl phthalic anhydride was synthesized from 4-bromophthalic anhydride and phenyl acetylene. The resultant 4-phenyl ethynyl phthalic anhydride was pale yellow crystalline powder. Physical properties were as follows (measurement conditions were the same as those in Example 3). The yield of the product was 82.3%:

Melting point: 151.1 to 151.8° C.;

Turbidity: 10.5 ppm;

Visible light absorption: 0.050 (400 nm), 0.022 (450 nm); and

GC purity: 98.7%.

Comparative Example 3

Synthesis of 4-phenyl ethynyl phthalic anhydride by Using the Method as Described in Non-Patent Document No. 2

In accordance with the method as described in Non-Patent Document No. 2 (Polymer, vol. 35, pp. 4858, 1994), 4-phenyl ethynyl phthalic anhydride was synthesized from 4-bromophthalic anhydride and phenyl acetylene. The resultant 4-phenyl ethynyl phthalic anhydride was pale yellow crystalline powder. Physical properties were as follows (measurement conditions were the same as those in Example 3). The yield of the product was 70.6%:

Melting point: 150.5 to 151.1° C.;

Turbidity: 12.1 ppm;

Visible light absorption: 0.049 (400 nm), 0.023 (450 nm); and

GC purity: 98.8%.

Example 5

Synthesis of Imide Oligomer by Using 4-phenyl ethynyl phthalic anhydride Obtained in Example 3 and Comparative Examples 1 to 3 as Terminal End Groups In accordance with the method as described in Non-Patent Document No. 2, a solution of an amide-acid oligomer having an average molecular weight of about 9,000 was prepared from the 4-phenyl ethynyl phthalic anhydrides obtained in Example 3 and Comparative Examples 1 to 3, and 3,4'-oxydianiline and an N-methyl pyrrolidone solution of 4,4'-oxydiphthalic anhydride. The thus-prepared amide-acid oligomer was centrifuged, applied, dried and subjected to thermal treatments for one hour at 100° C., 225° C. and 350° C. in this order, to thereby obtain films of cross-linked imide oligomer. On the other hand, toluene was added to an N-methyl pyrrolidone solution of the amide-acid oligomer and, the mixture was subjected to the steps of azeotropic dehydration, cooling, filtration, rinsing with water and methanol in this order, and drying, to thereby isolate an imide oligomer.

Tg and kinetic properties at 23° C. of each film prepared in accordance with the above-described method corresponding to 4-phenyl ethynyl phthalic anhydrides obtained in Example 3 and Comparative Examples 1 to 3 were measured in accordance with a method as specified in ASTM D882 and, also a temperature at which 5% by mass of the imide oligomer was reduced was measured by using a thermobalance. These results are shown in Table 1.

TABLE 1

| Production method for 4-phenyl ethynyl phthalic anhydride | Film of cross-linked imide oligomer (23° C.) | | | | Temperature of 5% mass reduction |
|---|---|---|---|---|---|
| | Tg | Tensile strength | Elastic modulus | Elongation at break | |
| Example 3 | 252° C. | 122.2 MPa | 3.0 GPa | 55% | 518° C. |
| Comparative Example 1 | 250° C. | 120.1 Mpa | 2.6 GPa | 31% | 514° C. |
| Comparative Example 2 | 252° C. | 118.8 MPa | 2.8 GPa | 36% | 511° C. |
| Comparative Example 3 | 251° C. | 119.7 MPa | 2.7 GPa | 36% | 514° C. |

As is apparent from Table 1, it is found that the 4-phenyl ethynyl phthalic anhydride obtained by the production method according to the present invention has a high purity and contains an extremely small amount of impurities and the obtained film, by using the 4-phenyl ethynyl phthalic anhydride as a terminal end-blocking material, is excellent so that the film has a high value of tensile strength, elastic modulus, elongation at break and temperature for 5% mass reduction. Further, when the above-described films were prepared ten times by using the 4-phenyl ethynyl phthalic anhydride obtained in Example 3, generation of a slightly soluble component and foaming at the time of forming or curing were not observed in any of the films. In contrast to the above, when the 4-phenyl ethynyl phthalic anhydrides obtained in Comparative Examples 1 to 3 were used, generation of a slightly soluble component and foaming at the time of forming or curing were sometimes observed.

Example 6

Synthesis of 4-(3-fluorophenylethynyl)dimethyl phthalate

Under a nitrogen gas stream, 10.9 g of 4-bromo-dimethyl phthalate, 5.8 g of 3-fluoroethynyl benzene, 28 mg of triphenylphosphine, 7.6 mg of trans-dichloro-bis (triphenylphosphine)palladium (II) and 6.2 mg of cuprous iodide were placed in a three-necked flask of 100-ml capacity at room temperature and 20 ml of triethylamine was then poured therein while being stirred. A reaction mixture was heated and refluxed by heating at 120° C. for 3 hours, cooled to 70° C. and, thereafter, the resultant reaction solution was filtered to remove generated salts and catalysts and, then, rinsed with 20 ml of toluene. The filtrate and a rinsing solution were combined and concentrated to obtain 14.2 g of an oily substance containing 4-(3-fluorophenyethynyl)dimethyl phthalate. The oily substance was recrystallized from a mixed solvent containing 2-propanol/hexane (20 ml/400 ml), and 9.93 g of 4-(3-fluorophenyethynyl)dimethyl phthalate was obtained. The yield thereof was 79.5%.

The physical properties of the product thus obtained were as follows:

$^1$H-NMR δ(TMS, CDCl$_3$): 3.92 ppm (s, 3H), 3.93 ppm (s, 3H), 7.05-7.12 ppm (m, 1H), 7.21-7.25 ppm (m, 1H), 7.30-7.38 ppm (m, 2H), 7.66 ppm (dd, 1H), 7.85 ppm (d, 1H)

Example 7

Compound No. 23: Synthesis of 4-(3-fluorophenylethynyl)disodium phthalate 109.3 g of 4-(3-3-fluorophenylethynyl)dimethyl phthalate and 175 ml of water were placed in a three-necked flask of 500 ml capacity to form a suspension, and 123 g of a 25% aqueous sodium hydroxide solution was added dropwise thereto with stirring. The reaction mixture was stirred at 75° C. for 3 hours and the completion of the reaction was confirmed. The temperature inside the flask was cooled to 30° C., and 5 g of active carbon was added thereto, and the temperature of the mixture was maintained at the same temperature with stirring. The active carbon was removed by filtration by using Celite as a filter aid. After rinsing, the filtrate and a rinsing solution were combined, and 500 ml of 2-propanol was added dropwise thereto over 30 minutes with stirring to precipitate 4-(3-fluorophenylethynyl)disodium phthalate. After stirring in an iced bath for two hours, filtering, washing and drying, 103.4 g of a white crystal of 4-(3-fluorophenylethynyl)disodium phthalate was obtained. The yield thereof was 90.0%.

The physical properties of the product thus obtained were as follows:

IR vmax (KBr): 3422 (m), 2362 (w), 2341 (m), 1633 (w), 1576 (vs), 1481 (m), 1420 (s), 1369 (m), 1148 (w), 870 (m), 835 (m), 806(m) cm$^{-1}$;

Example 8

Compound No. 24: Synthesis of 4-(3-fluorophenylethynyl)phthalic acid 109.3 g of 4-(3-3-fluorophenylethynyl)dimethyl phthalate and 175 ml of water were placed in a three-necked flask of 500 ml capacity to form a suspension, and a 25% aqueous sodium hydroxide solution was added dropwise thereto with stirring. The reaction mixture was stirred at 75° C. for 3 hours and the completion of the reaction was confirmed. The temperature inside the flask was cooled to 30° C., and 5 g of active carbon was added thereto, and the temperature of the mixture was maintained at the same temperature with stirring. The active carbon was removed by filtration by using Celite as a filter aid. After rinsing, the filtrate and a rinsing solution were combined and 600 ml of ethyl acetate was added thereto, and thereafter 86.3 g of concentrated hydrochloric acid was added with heating and stirring. 4-(3-fluorophenylethynyl)phthalic acid was precipitated once, and dissolved. When stirring was stopped, the mixture was separated into two phases, and the water phase was removed. The ethyl acetate solution was concentrated under reduced pressure and removed, so that 114.2 g of a crude crystal of 4-(3-fluorophenylethynyl)phthalic acid was obtained. 250 ml of 2-propanol was added to the crude crystal, and placed in a three-necked flask of 1 liter. The temperature inside of the flask was increased to 50° C. with stirring, and 500 ml of water was added thereto. Thereafter, the suspension thus formed was cooled to 20° C. over 3 hours. After the temperature inside of the flask reached at 20° C., stirring was continued for 1 hour, followed by filtering, washing and drying, to obtain 93.8 g of 4-(3-fluorophenylethynyl)phthalic acid was obtained.

The physical properties of the product thus obtained were as follows:

Melting point: 194.4° C. (Dehydrated to form 4-(3-fluorophenylethynyl)phthalic anhydride due to heating)

$^1$H-NMR δ(TMS, dimethyl sulfoxide-d$_6$): 7.30-7.36 ppm (m, 1H), 7.48 ppm (s, 1H), 7.50-7.52 ppm (m, 2H) 7.60 ppm (s, 2H), 7.48 ppm (s, 1H) IR vmax (KBr): 2885 (m), 2364 (w), 1706 (vs), 1920 (m), 864 (m), 842 (m), 791 (s), 683 (m) cm$^{-1}$;

Example 9

Compound No. 18: Synthesis of
4-(3-fluorophenylethynyl)phthalic anhydride Using
4-(3-fluorophenylethynyl)dimethyl phthalate
(Straight Method without Isolating Dicarboxylic
Acid)

109.3 g of 4-(3-3-fluorophenylethynyl)dimethyl phthalate and 175 ml of water were placed in a three-necked flask of 500 ml capacity to form a suspension, and 123 g of a 25% aqueous sodium hydroxide solution was added dropwise thereto with stirring. The reaction mixture was stirred at 75° C. for 3 hours and the completion of the reaction was confirmed. The temperature inside the flask was cooled to 30° C. and 5 g of active carbon was added thereto, and the temperature of the mixture was maintained at the same temperature with stirring. The active carbon was removed by filtration by using Celite as a filter aid. After rinsing, the filtrate and a rinsing solution were combined and 400 ml of methyl ethyl ketone was added, and thereafter 86.3 g of concentrated hydrochloric acid was added with heating and stirring. 4-(3-fluorophenylethynyl)phthalic acid was precipitated once, and dissolved. When stirring was stopped, the mixture was separated into two phases, and the water phase was removed. After the organic phase was partially concentrated, 80.1 g of acetic anhydride was added thereto and the reaction mixture was heated and refluxed for 4 hours. When the reaction mixture was cooled, 4-(3-fluorophenylethynyl) phthalic anhydride was precipitated as a crystal. The crystal was filtered, washed and dried to obtain 80.2 g of a pale yellow crystal of 4-(3-fluorophenylethynyl)phthalic anhydride. The yield thereof was 86.1% based on 4-(3-3-fluorophenylethynyl)dimethyl phthalate.

The physical properties of the product thus obtained were as follows:

$^1$H-NMR δ(TMS, CDCl$_3$): 7.11-7.18 ppm (m, 1H), 7.26-7.29 ppm (s, 1H), 7.36-7.40 ppm (m, 2H), 8.00 ppm (s, 2H), 8.13 ppm (s, 1H) IR vmax (KBr): 3065 (w), 2352 (w), 2212 (w), 1850 (s), 1778 (vs), 1661 (s), 1576 (m), 1427 (m), 1327 (m), 1250 (vs), 920 (s), 885 (m), 737 (s) cm$^{-1}$;

Turbidity: 0.1 ppm (measurement conditions are the same as those of Example 3)

GC purity: 99.9% or more (GC conditions: column; (manufactured by J&W Scientific) DB-5MS; 0.53 mm×30 m; carrier gas, helium 70 kPa; sprit ratio, 1:40; detection, FID, column temperature, 100° C.→300° C.; temperature increase (10° C./min.)

Example 10

Compound No. 18: Synthesis of
4-(3-fluorophenylethynyl)phthalic anhydride Using
4-(3-fluorophenylethynyl)phthalic acid 85.3 g of 4-(3-3-fluorophenylethynyl)phthalic acid, 200 ml of toluene and 45.9 g of acetic anhydride were placed in a three-necked flask of 500 ml capacity in this order, and the mixture heated at 120° C. with stirring to form a suspension. After it was confirmed that reflux started at the temperature of 114° C. in the suspension, the reflux was continued for one hour to proceed the reaction. The solution, in which the starting materials were dissolved, formed by the reaction was cooled to 3° C. over 3 hours to precipitate the reaction product. The precipitate was filtered, washed and dried to obtain 70.2 g of an extremely pale yellow crystal of 4-(3-fluorophenylethynyl)phthalic anhydride. The physical properties of the product were as follows:

Melting point; 142.9° C.

NMR and IR data: coincided with the data obtained in those of Example 9;

Turbidity; 0.4 ppm (measurement conditions were the same as those of Example 3; and GC purity; 99.9% or more (measurement conditions were the same as those of Example 9.

Example 11

Compound No. 9: Synthesis of
4-(3-fluorophenylethynyl)dimethyl phthalate 136.54 g of 4-bromodimethyl phthalate, 69.7 g of 4-ethynyl toluene, 354 mg of triphenylphosphine, 94.8 mg of trans-dichloro-bis(triphenyphosphine)paradium (II) and 771 mg of cuprous iodide were placed in a three-necked flask of 1 liter capacity, and 101.2 g of triethylamine was further added while stirring. The reaction mixture was refluxed by heating at 110° C. while being stirred for 6 hours, and the temperature inside the flask was cooled to 60° C. The reaction solution was filtered to remove the catalysts and the formed salt, and washed with 200 ml of toluene. The filtrate and a rinsing solution were combined and concentrated to obtain 25.1 g of a crude crystal of 4-(4-methylphelethynyl) dimethyl phthalate. The crude crystal was recrystallized from a mixed solvent containing 2-propanol and n-hexane (½ by volume) to obtain 133.8 g of 4-(4-methylphelethynyl) dimethyl phthalate. The yield of the product was 86.8%.

The physical properties of the product thus obtained were as follows:

$^1$H-NMR δ(TMS, CDCl$_3$): 2.38 ppm (s, 3H), 3.92 ppm (s, 3H), 3.93 ppm (s, 3H), 7.18 ppm (d, 2H), 7.43 ppm (d, 2H), 7.64 ppm (dd, 1H), 7.74 ppm (d, 1H), 7.83 ppm (d, 1H).

Example 12

Compound No. 17: Synthesis of
4-(4-methylphenylethynyl)phthalic anhydride Using
4-(4-methylphenylethynyl)dimethyl phthalate
(Method of Isolating Dicarboxylic Acid)

123.6 g of 4-(4-methylphenylethynyl)dimethyl phthalate was suspended in 200 g of water, and 141 g of an aqueous 25% by mass sodium hydroxide solution was added dropwise thereto while being stirred. The reaction mixture was stirred at 65° C. for 2 hours. After confirming the completion of the reaction, the temperature inside the flask was cooled to 30° C. and 10 g of active carbon was added thereto. The reaction mixture was stirred at the same temperature for 30 minutes, and filtered to remove the active carbon. The filtrate and a rinsing solution were combined, and 98.6 g of concentrated hydrochloric acid (35.5% by mass) was added dropwise thereto. 500 ml of methyl ethylketone was added to the reaction mixture, and the mixture was heated at 60° C. for 30 minutes, and allowed to stand. The water phase was removed and concentrated to obtain 1 μg of a crude crystal of 4-(4-methylphenylethynyl)dimethyl phthalic acid. This product was recrystallized from a mixed solvent containing 2-propanol and distilled water (¼ by volume) to obtain 95.63 g of a colorless crystal of 4-(4-methylphenylethynyl) phthalic acid. 84 g out of the crystal thus obtained was suspended in toluene, and 46 g of acetic anhydride was added thereto, and the resultant reaction mixture was refluxed by heating for 2 hours. After termination of the reaction, the mixture was cooled to precipitate a crystal of 4-(4-methylphenylethynyl)phthalic anhydride. The crystal was filtered, washed and dried to obtain 71.6 g of a pale yellowish green crystal of 4-(4-methylphenylethynyl)phthalic anhydride. The yield of the product was 77.6% based on 4-(4-methylphenylethynyl)dimethyl phthalate.

The physical properties of the obtained product were as follows:

$^1$H-NMR δ(TMS, CDCl$_3$): 2.40 ppm (s, 3H), 7.20 ppm (d, 2H), 7.45 ppm (dd, 2H), 7.96 ppm (s, 1H), 7.96 ppm (s, 1H), 8.07 ppm (t, 1H) IR vmax (KBr): 2920 (w), 2214 (w), 1840 (w), 1776 (vs), 1611 (m), 1508 (w), 1321 (m), 1246 (s), 930 (m), 889 (s), 818 (s), 737 (s), 671 (m), 523 (m) cm$^{-1}$ Turbidity: 0.0 ppm (measurement conditions are the same as those of Example 3)

Visible light absorbance: 0.153 (400 nm); 0.001 (450 nm) (measurement conditions are the same as those of Example 3)

GC purity: 99.9%.

What is claimed is:

1. An aryl ethynyl phthalic acid diester compound, represented by the following Formula 3:

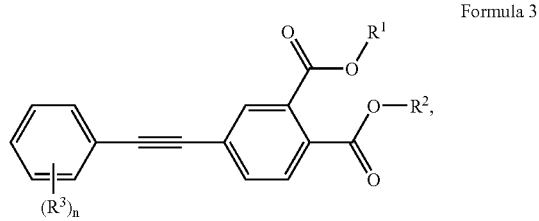

Formula 3 wherein $R^1$ and $R^2$ each independently represent an alkyl group having 1 to 8 carbon atoms, a cycloalkyl group or an aryl group; $R^3$ represents a halogen atom, a hydroxyl group, an alkyl group having 1 to 10 carbon atoms, a cycloalkyl group having 3 to 10 carbon atoms, an aryl group having 6 to 12 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms or a perfluoroalkoxy group having 1 to 6 carbon atoms; n represents an integer of from 0 to 2; and when n represents 2, such that $R^3$ is present in plurality, each $R^3$ may be the same as or different from any other $R^3$ or linked thereto to form a ring.

2. An aryl ethynyl phthalic acid diester compound, represented by the following Formula 3:

Formula 3 wherein $R^1$ and $R^2$ each independently represent an alkyl group having 1 to 8 carbon atoms, a cycloalkyl group or an aryl group; $R^3$ represents a halogen atom, a hydroxyl group, an alkyl group having 1 to 10 carbon atoms, an aryl group having 6 to 10 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms or a perfluoroalkoxy group having 1 to 6 carbon atoms; n represents an integer of from 0 to 2; and when n represents 2, such that $R^3$ is present in plurality, each $R^3$ may be the same as or different from any other $R^3$ or linked thereto to form a ring.

3. A method for producing an aryl ethynyl phthalic anhydride represented by the following Formula 5, comprising:

hydrolyzing an aryl ethynyl phthalic acid diester compound represented by the following Formula 3 to provide an aryl ethynyl phthalic acid compound represented by the following Formula 4, and subjecting the aryl ethynyl phthalic acid compound represented by the following Formula 4 to ring-closing:

Formula 3

Formula 4

Formula 5 wherein $R^3$ represents a halogen atom, a hydroxyl group, an alkyl group having 1 to 10 carbon atoms, an aryl group having 6 to 10 carbon atoms, an alkoxy group having 1 to 6 carbon atoms, an aryloxy group having 6 to 12 carbon atoms, an acyl group having 1 to 10 carbon atoms, a perfluoroalkyl group having 1 to 6 carbon atoms or a perfluoroalkoxy group having 1 to 6 carbon atoms; n represents an integer of from 0 to 5; and when n represents 2 or more, such that $R^3$ is present in plurality, each $R^3$ may be the same as or different from any other $R^3$ or linked thereto to form a ring and wherein, in Formula 3, $R^1$ and $R^2$ each independently represent an alkyl group having 1 to 8 carbon atoms, a cycloalkyl group or an aryl group.

4. A method for producing an aryl ethynyl phthalic anhydride represented by Formula 5 according to claim 3, wherein the hydrolysis is alkali hydrolysis in which a reaction mixture obtained by hydrolyzing the aryl ethynyl phthalic acid diester compound represented by Formula 3 is subjected to an adsorbent treatment followed by addition of an acid to obtain an aryl ethynyl phthalic acid compound represented by Formula 4.

5. A method for producing an aryl ethynyl phthalic anhydride as represented by Formula 5 according to claim 4, wherein the adsorbent treatment is an adsorbent treatment using active carbon.

6. A fluorine-containing aryl ethynyl phthalic acid or salt thereof represented by Formula 4A:

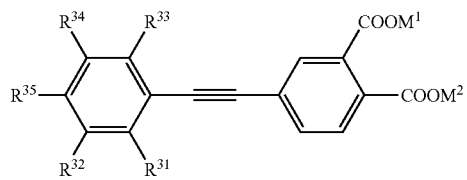

Formula 4A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and $M^1$ and $M^2$ each independently represent a hydrogen atom or a metal atom.

7. A fluorine-containing aryl ethynyl phthalic acid or salt thereof represented by Formula 4A according to claim 6, wherein: (1) when any one of $R^{31}$, $R^{32}$, $R^{33}$, $R^{34}$ and $R^{35}$ represents a fluorine atom, the remaining groups are hydrogen atoms; (2) when $R^{31}$ represents a trifluoromethyl group, $R^{32}$, $R^{33}$, $R^{34}$ and $R^{35}$ are hydrogen atoms; or (3) when $R^{32}$ represents a trifluoromethyl group, $R^{31}$, $R^{33}$, $R^{34}$ and $R^{35}$ represent hydrogen atoms.

8. A method for producing a fluorine-containing aryl ethynyl phthalic anhydride represented by the following Formula 5A obtained by subjecting a fluorine-containing aryl ethynyl phthalic salt represented by the following Formula 4A to ring-closing:

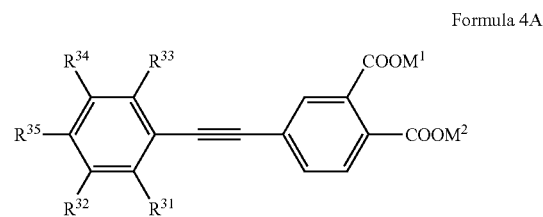

Formula 4A

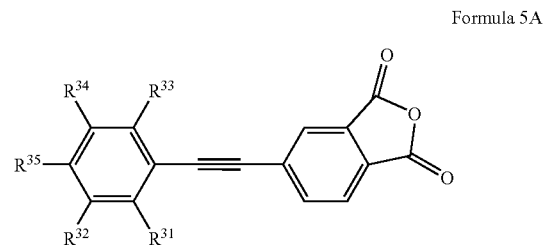

Formula 5A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and $M^1$ and $M^2$ each independently represent a metal atom.

9. A method for producing a fluorine-containing aryl ethynyl phthalic salt represented by the following Formula 4A obtained by subjecting a fluorine-containing aryl ethynyl phthalic acid diester compound represented by the following Formula 3A to hydrolysis:

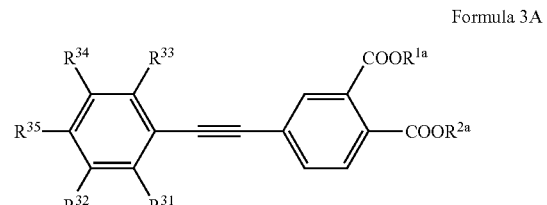

Formula 3A

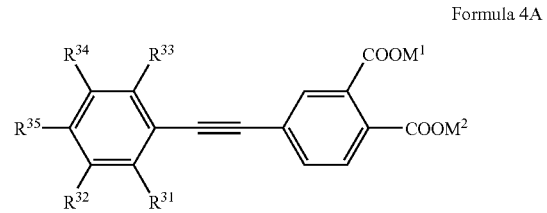

Formula 4A wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; $M^1$ and $M^2$ each independently represent a metal atom, and $R^{1a}$ and $R^{2a}$ each independently represent an alkyl group.

10. A method according to claim 8, wherein the fluorine-containing aryl ethynyl phthalic salt represented by Formula 4A is obtained by subjecting a fluorine-containing aryl ethynyl phthalic acid diester compound represented by the following Formula 3A to hydrolysis:

Formula 3A

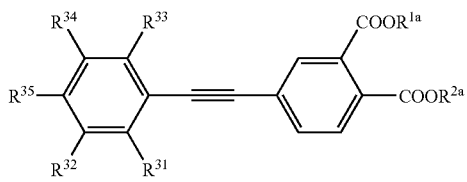

wherein $R^{31}$, $R^{32}$, $R^{33}$, $R^{34}$ and $R^{35}$ each independently represent a hydrogen atom, a fluorine atom or a trifluoromethyl group; $R^{31}$, $R^{32}$, $R^{33}$, $R^{34}$ and $R^{35}$ are neither all hydrogen atoms nor all fluorine atoms at the same time; when $R^{31}$, $R^{32}$, $R^{33}$ and $R^{34}$ are hydrogen atoms, $R^{35}$ is a fluorine atom; and $R^{1a}$ and $R^{2a}$ each independently represent an alkyl group.

* * * * *